United States Patent [19]
Woodward

[11] Patent Number: 5,035,147
[45] Date of Patent: Jul. 30, 1991

[54] METHOD AND SYSTEM FOR DIGITAL MEASUREMENT OF ACOUSTIC BURST TRAVEL TIME IN A FLUID MEDIUM

[75] Inventor: William S. Woodward, Chapel Hill, N.C.

[73] Assignee: Curtin Matheson Scientific, Inc., Houston, Tex.

[21] Appl. No.: 478,101

[22] Filed: Feb. 9, 1990

[51] Int. Cl.$^5$ .......................... G01F 1/66; G01H 5/00
[52] U.S. Cl. .................................. 73/861.28; 73/597; 73/861.29
[58] Field of Search ........... 73/861.27, 861.28, 861.29, 73/597

[56] References Cited

U.S. PATENT DOCUMENTS

| | | |
|---|---|---|
| 3,738,169 | 6/1973 | Courty . |
| 3,901,078 | 8/1975 | McShane . |
| 4,162,630 | 7/1979 | Johnson .......................... 73/861.27 |
| 4,384,491 | 5/1983 | Brown et al. .................... 73/861.28 |
| 4,452,090 | 6/1984 | Kou et al. . |
| 4,611,496 | 9/1986 | Komachi . |

OTHER PUBLICATIONS

"Ultrasonic Measurements for Process Control", Theory, Techniques, Applications, Lynnworth, Academic Press, Inc. Harcourt Brace Jovanovich, Publishers, pp. 17 and 19.

Primary Examiner—Charles A. Ruehl
Attorney, Agent, or Firm—Townsend & Townsend

[57] ABSTRACT

Fluid flow along a fluid path is determined by measuring the travel time between two transducers of two oppositely travelling acoustic burst waves. A pair of phase reference signals in phase quadrature are compared with the signals received by each transducer to determine the phase difference therebetween. The phase difference values are used to calculate the flow velocity.

After each phase difference determination has been made, the transducer drive signals are adjusted so that the launch time of the next pair of burst waves reduces the phase difference between the previously received signals and the phase reference to zero in the absence of any changes in flow velocity. The duration of each acoustic burst is sufficient to ensure that a predetermined number of successively received cycles in each burst are used in the phase comparison process.

24 Claims, 2 Drawing Sheets

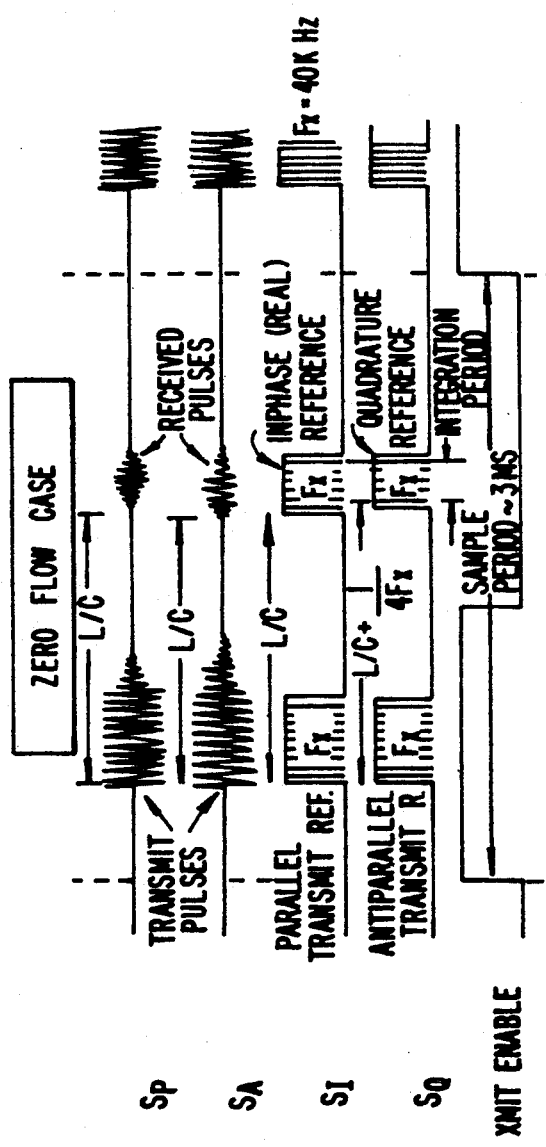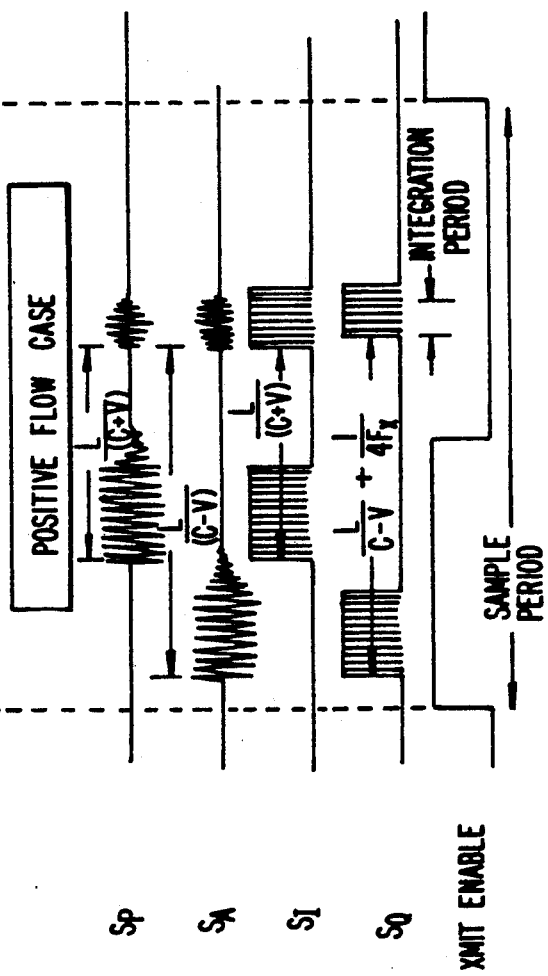

METHOD AND SYSTEM FOR DIGITAL MEASUREMENT OF ACOUSTIC BURST TRAVEL TIME IN A FLUID MEDIUM

BACKGROUND OF THE INVENTION

This invention relates to the field of fluid flow velocity measurement.

Various types of flowmeters have been utilized in the past for measuring the time of flight of an acoustic signal between a pair of spaced transducers. Typical examples of such systems are U.S. Pat. Nos. 4,452,090; 3,901,0778; 3,738,169; and 4,611,496. In general, acoustic or ultrasonic pulses are transmitted either alternately or simultaneously in the downstream and the upstream directions between two transducers. The travel time in the downstream direction and in the upstream direction is determined and the two resulting values are combined to either determine the flow velocity value or the speed of sound in the fluid medium. This information can also be used to determine the composition of a binary gas mixture assumed to be motionless. Both analog and digital systems have been designed for this purpose, with varying degrees of success.

Known devices of the above type suffer from several disadvantages. Firstly, many of the analog devices are highly susceptible to signal noise and drift, particularly in those applications in which the environment is quite noisy and subject to changing ambient conditions. Although digital devices tend to be less susceptible to noise, lack of stability is still a problem with such devices. In addition, most known devices suffer from a limited dynamic range which is not well suited to a wide variety of applications or to particular applications in which the flow velocities are subject to wide variation (e.g., in a spirometry application). Further, known devices suffer from a limited measurement accuracy due to a variety of factors, including phase changes or frequency changes in the acoustic signal during transmission and reception, between sample changes of a magnitude greater than the ability of the measurement apparatus to unambiguously detect, and relatively low resolution capability.

SUMMARY OF THE INVENTION

The invention comprises a method and apparatus for determining the intertransducer travel time of a pair of bursts of acoustic signals which is devoid of the above-referenced disadvantages and which is relatively inexpensive to implement and highly reliable in operation.

From a method standpoint, the invention comprises a method of determining the travel time of an acoustic wave in a fluid including the steps of generating a pair of bursts of acoustic waves at two different locations in a fluid medium, establishing a phase reference, receiving each burst at a location different from the generation location for that burst, comparing portions of each received burst with the phase reference to determine the phase therebetween, selecting a phase value for each burst to be next generated in each location which reduces any phase difference between the previously received burst and the phase reference to a substantially zero value, and using the phase comparison result to determine the travel time. Each burst has a predetermined frequency, and the phase comparison is carried out on N successive cycles of a given burst, where N is an integer.

Preferably, the phase references established according to the method are a pair of references in phase quadrature, and the phase comparison is conducted with respect to both references.

From a system standpoint, the invention includes transducer means for generating successive pairs of bursts of acoustic waves at two different locations in a fluid medium and for receiving the bursts after travel through the fluid medium, means for establishing a phase reference, means for comparing portions of each received burst with the phase reference to determine the phase therebetween, means for selecting a phase value for each burst to be next generated by the transducer means which reduces any phase difference between the received burst portion and the phase reference to substantially zero value, and means for storing the phase determination result obtained by the comparing means. The phase reference establishing means preferably includes means for generating a pair of references in phase quadrature, and the comparing means preferably includes means for comparing portions of each received burst with each phase quadrature reference.

The comparing means preferably includes phase detector means having a first input coupled to the phase reference establishing means, a second input coupled to the transducer means, and an output, and means coupled to the output of the phase detector means for generating an accumulated value representative of the phase difference. Each phase detector means includes a pair of phase detector circuits, and the second input of each of the pair of phase detector circuits receives a different one of the pair of bursts from the transducer means.

The transducer means preferably includes a pair of transducers each positioned at a different one of the two different locations, and each of the pair of phase detector circuits is coupled to a different one of the pair of transducers.

The phase reference establishing means further includes an oscillator means for generating a relatively high frequency clock signal, and programmable timer means coupled to the oscillator means for generating a phase reference signal. The programmable timer means preferably includes first and second programmable timer circuits for generating a pair of phase reference signals in phase quadrature. The programmable timer means also includes means for generating a transducer drive signal having a frequency matched to the acoustic waves, and the system further preferably includes means for periodically coupling the output of the programmable timer means to the transducer means to generate the pairs of bursts. The coupling means includes a pair of switch means each coupled between an associated one of the programmable timer circuits and an associated one of the pair of transducers for periodically supplying the transducer drive signal from the associated programmable timer circuit to the associated transducer.

In a more specific system aspect, the invention includes first and second transducer means for transmitting and receiving acoustic bursts through a fluid along a fluid path, one of the transducer means being positioned adjacent a first location in the fluid path, the other one of the transducer means being positioned adjacent a second location in the fluid path spaced from the first location, each transducer means being arranged to receive the acoustic bursts transmitted by the other transducer means and travelling through the fluid path and to convert the received bursts to equivalent burst signals; means for generating a plurality of system signals including a pair of phase reference signals in phase quadrature and drive signals for the first and second transducer means; means for periodically coupling the drive signals to the first and second transducer means; means coupled to the transducer means and the generating means for comparing the equivalent burst signals from the first and second transducer means to the pair of phase reference signals to determine the phase difference therebetween; feedback means coupled to the comparing means and the generating means for adjusting the phase of the drive signals to reduce the determined phase difference to a value of substantially zero; and means for computing the value of the fluid flow along the fluid path between the first and second transducer means from the determined phase difference between the received burst and the pair of phase reference signals.

The comparing means preferably includes four phase detectors arranged in pairs, with one pair dedicated to the received signals from one of the transducer means and the other pair dedicated to the received signals from the other transducer means. Each phase detector has a second phase reference input supplied by the system signal generating means and an output coupled to an associated digital accumulator which accumulates a count over several successive cycles of the received transducer signals, the count being representative of the phase difference between the received signals and the phase reference signal associated to that accumulator.

The invention provides a travel time measurement system of extremely high accuracy, fine resolution, wide dynamic range and relatively low vulnerability to noise signals.

For a fuller understanding of the nature and advantages of the invention, reference should be had to the ensuing detailed description taken in conjunction with the accompanying drawings.

BRIEF DESCRIPTION OF THE DRAWINGS

FIGS. 2A and 2B are representative wave form diagrams illustrating the operation of the system of FIG. 1.

DESCRIPTION OF THE PREFERRED EMBODIMENTS

Figure 1:
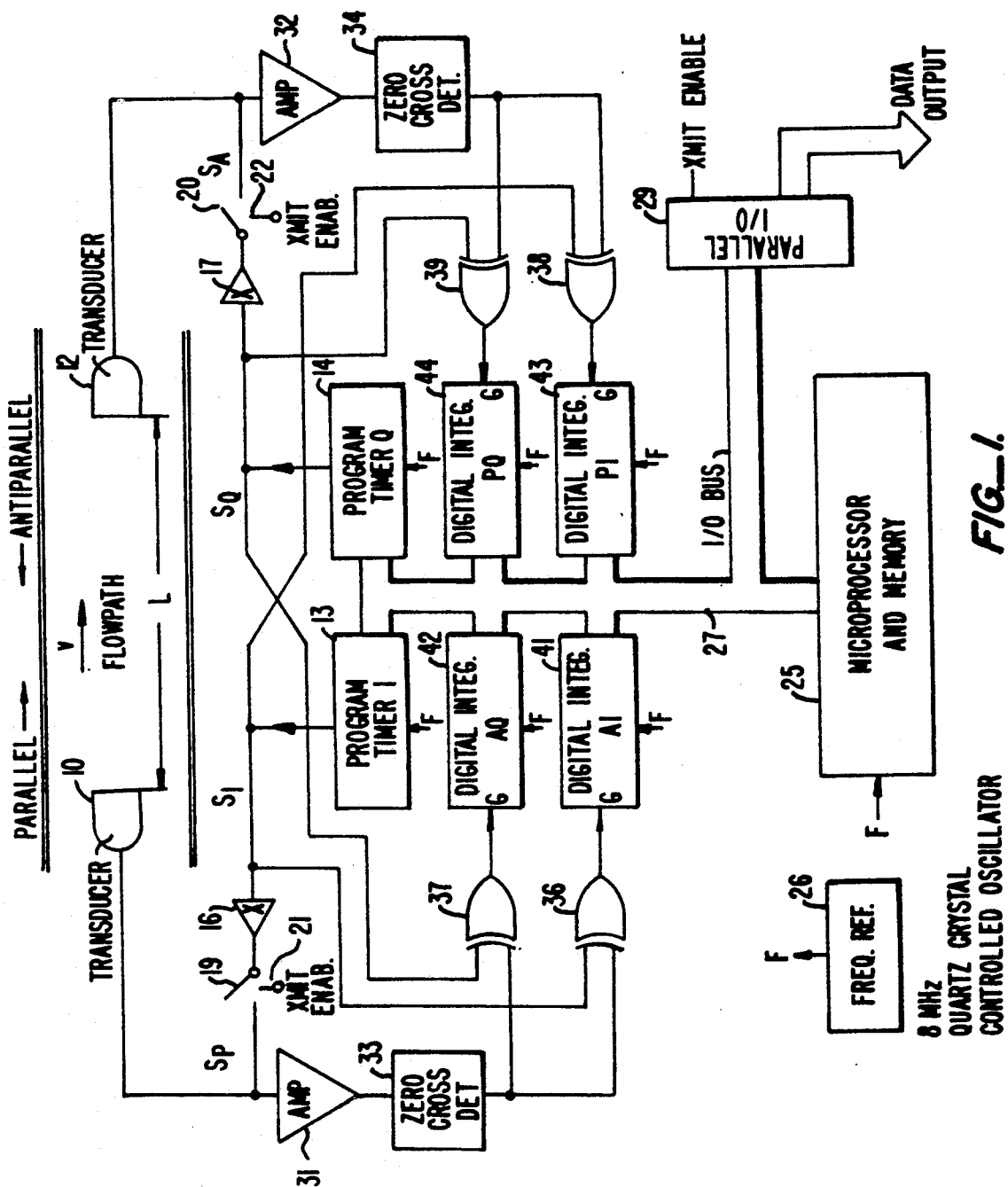
FIG. 1 is a block diagram illustrating a preferred embodiment of a system fabricated according to the invention.

Turning now to the drawings, FIG. 1 is a block diagram illustrating a preferred embodiment of a system incorporating the invention. As seen in this Fig., a pair of transducers 10, 12 are arranged along a flow path and are separated by a constant distance L. Transducers 10, 12 may comprise any suitable transducer capable of generating a burst of acoustic waves of a predetermined frequency over a desired repetition rate range in a fluid medium. Since such transducers are well known to those skilled in the art, they will not be further described. In the preferred embodiment, acoustic waves generated by transducers 10, 12 comprise a burst of about 20 cycles of a 40 khz signal, with the repetition rate of each burst being in the range from around zero to 300 hz. These values have been found to be useful for spirometer applications of the invention.

As seen in FIG. 1, any fluid flow along the flow path occurs at a velocity v, and one purpose of the invention is to measure this value. As described more fully below, fluid flow v is measured by determining the travel time of each burst from transducer 10 to transducer 12 in the parallel direction (left to right in FIG. 1) and from transducer 12 to transducer 10 in the anti-parallel direction (from right to left in FIG. 1). It is understood that the flow path may be any conduit such as a spirometer tube or the like through which fluid can flow at a velocity v.

Each one of transducers 10, 12 is operated in both a transmit mode and a receive mode. Ideally, under zero flow conditions, each transducer 10, 12 will be operated in the transmit mode simultaneously to create an acoustic burst at each location simultaneously. When there is flow along a given direction (such as the parallel direction illustrated), the transducers 10, 12 are operated in the transmit mode at different times as part of the novel functioning of the invention.

Each transducer is also operated in a receive mode for a sufficient period of time to detect the acoustic burst flowing along the flow path from the opposite transducer. The received acoustic bursts are converted to equivalent electrical signals having the same frequency and phase as the acoustic burst waves received.

Each transducer 10, 12 is driven in the transmit mode by an associated programmable timer 13, 14 via an associated buffer amplifier 16, 17 and an associated transmit switch 19, 20 operated by a separate transmit enable signal supplied by a microprocessor unit 25. Each programmable timer 13, 14 is provided with a high frequency (8 mhz) frequency reference F supplied by a system oscillator 26, preferably a quartz crystal controlled oscillator. Each programmable timer 13, 14 is also provided with appropriate control signals from the microprocessor unit 25 via system bus 27. Each timer 13, 14 has a dual function: firstly, to generate the 40 khz transmit signals supplied to the associated transducer; and secondly to provide phase reference signals $S_i$ and $S_q$ used to establish the acoustic burst travel times along the flow path in a manner described below. The phase reference signals $S_i$ and $S_q$ are also 40 khz signals and are arranged in phase quadrature, i.e., reference signal $S_q$ is phase displaced from reference signal $S_i$ by 90°.

In the receive mode, the output signals generated by transducer 10, 12 in response to received acoustic bursts are coupled via dedicated amplifiers 31, 32 to associated zero crossing detectors 33, 34 in which the received equivalent signals are squared up to produce binary wave trains corresponding to the received signals. The output of each zero crossing detector 33, 34 is coupled to an associated pair of phase detectors in the following manner. The output signals from zero crossing detector 33, representing the received signals corresponding to the acoustic burst originally transmitted by transducer 12, are coupled as a first input to a pair of phase detectors 36, 37, which in the preferred embodiment are a pair of exclusive OR gates. The other input to phase detector 36 is the zero phase reference signal $S_i$ supplied by programmable timer 13; the other input to phase detector 37 is the quadrature reference signal $S_q$ from programmable timer 14. Similarly, the output of zero crossing detector 34 representing the received version of the acoustic burst originally generated by transducer 10 is coupled to a first input of a pair of associated phase detectors 38, 39. The other input to phase detector 38 is the phase reference signal $S_i$; while the other input to phase detector 39 is the quadrature phase reference signal $S_q$.

The output of phase detector 36 is coupled to the gating input of a first digital integrator 41, which is a high speed incrementable counter in the preferred embodiment. The sample clock or count input to integrator 41 is the high frequency reference signal generated by oscillator 26. In a similar fashion, a digital integrator 42 has a clock input for receiving the high speed clock signal F and a gating input to receive the output of phase detector 37. Digital integrators 43 and 44 are similarly arranged to receive the high speed clock input F and the output from phase detectors 38, 39, respectively.

Each digital integrator 41–44 is arranged to accumulate counts whenever a phase difference exists between the two inputs to the respective phase detector. Thus, digital integrator 41 accumulates counts over a comparison period which corresponds to the total phase difference between the phase reference signal $S_i$ and the signals received by transducer 10 from transducer 12; integrator 42 accumulates a count over a comparison period corresponding to the total phase difference between the quadrature phase reference signal $S_q$ and the signals received by transducer 10 from transducer 12; digital integrator 43 accumulates a count representative of the total phase difference between the phase reference signal $S_i$ and the signals received by transducer 12 from transducer 10; and integrator 44 accumulates a count representative of the total phase difference between the quadrature phase reference signal $S_q$ and the signals received by transducer 12 from transducer 10. Integrators 41–44 are under the control of microprocessor unit 25 via bus 27. In addition, the accumulated results at the end of a comparison period are transferred over bus 27 to the microprocessor unit 25 for computational purposes, and the results are output via bus 27 through a suitable I/O device 29 to any suitable follow-on unit, such as a strip chart recorder, a printer or the like.

The system of FIG. 1 is operated in such a manner that the travel time of an acoustic wave along the flow path between transducers 10 and 12 is measured in both directions to great accuracy (on the order of 4.0 nanoseconds for a 40 khz wave and a system frequency F of 8 mhz). These travel times in opposite directions are then used to compute values of interest, such as flow velocity, actual speed of sound, flow volume or the like. For example, to compute flow velocity, the following formula can be used:

$$v = \frac{L}{2}\left[\frac{1}{T_p} - \frac{1}{T_a}\right]$$

where v is flow velocity, L is the distance between transducers 10 and 12, $T_p$ is the wave travel time in the parallel direction between transducer 10 and transducer 12, and $T_a$ is the wave travel time between transducer 12 and transducer 10 in the anti-parallel direction. Similarly, speed of sound in the fluid can be calculated according to the following formula:

$$c = \frac{L}{2}\left[\frac{1}{T_p} + \frac{1}{T_a}\right]$$

where c equals the speed of sound in the fluid and the remaining variables have the same significance as noted above.

FIG. 2A illustrates representative system signals in the case of zero flow along the flow path. In this Fig., as well as FIG. 2B, the signal labelled $S_a$ is the acoustic signal generated in the anti-parallel direction, signal $S_p$ is the acoustic signal generated in the parallel flow path direction, signal $S_i$ represents the output from programmable timer 13 and signal $S_q$ represents the signal output from programmable timer 14. Also shown in FIG. 2A is the transmit enable signal which is active over the first half period of a sample period in the preferred embodiment. As can be seen in FIG. 2A, after the commencement of the sample period designated by the active level of the transmit enable signal, transducer 10 generates a 40 khz burst of acoustic waves $S_p$ over a period of time which is less than the duration of the transmit enable signal during the sample period. Similarly, in the zero flow case of FIG. 2A at the same time transducer 12 emits a burst of several cycles of acoustic waves Sa over essentially the same period. In both cases for each transducer the burst is generated in response to the receipt from the associated programmable timer of the 40 khz drive signal. This signal is generated by the associated timer 13, 14 for a predetermined number of cycles, which in the preferred embodiment is 20 cycles. The timer drive signals are illustrated directly below the transmit pulses in signals $S_i$ (timer 13 output) and $S_q$ (timer 14 output). As can be seen from the Fig., after the termination of the drive signals $S_i$ and $S_q$, each transducer 10, 12 continues to ring down for a measurable period of time, after which each transducer 10, 12 is ready to receive the acoustic burst travelling through the fluid along the flow path from the opposite transducer.

The pulses received by the transducers 10, 12 are shown in FIG. 2A to the right of the transmit pulses spaced by a distance equal to the flow path length L divided by the speed of sound c in the fluid. The transducers 10, 12 generate the electrical equivalent to the acoustic signals, which have the packet shape illustrated for signals $S_a$ and $S_p$. These signals are coupled to the respective phase detectors 36–39 where the phase of each signal is compared with the quadrature phase reference signals $S_i$ and $S_q$. The zero phase reference (the in-phase reference) is generated by timer 13, while the quadrature reference, (which differs in phase from the in-phase reference by +90°) is generated by timer 14. Each received burst packet is phase compared with both phase references over a predetermined number of 40 khz cycles. In the preferred embodiment, the number of cycles over which the phase comparison is conducted is 16 and these 16 cycles are selected by the microprocessor unit 25 to be centered about the expected central portion of the burst packet. Thus, in the zero flow case under ideal conditions, the 16 cycles over which the phase comparison is made comprise the 3rd through 18th cycles in the burst packet. For each cycle of a given burst packet the in-phase and quadrature digital integrators accumulate counts whenever an out-of-phase condition exists between the two inputs to each phase detector. Thus, for the burst packet received by transducer 10, integrator 41 accumulates counts whenever the received burst is out of phase with respect to the in-phase reference signal $S_i$, while integrator 42 accumulates counts whenever the received signal is out of phase with respect to the quadrature phase reference $S_q$. Since the phase comparison is conducted over a predetermined number of cycles, time varying effects are averaged. Thus, for example, if the actual frequency of the 40 khz signal within the burst packet varies at all over the 16 cycle comparison period, such variations will be averaged in the integrators 41, 42. The same is true with respect to the integrators 43, 44 and the signals received by transducer 12.

After the phase comparison is completed, the contents of the integrators 41-44 are examined to determine the phase difference between the received signals and the reference signals. Since the received signals are compared with quadrature related phase reference signals, not only the magnitude of the phase difference but also the direction can be determined. Consequently, the result of the examination of the contents of the digital integrators 41-44 by the microprocessor system 25 is a direct measure of the difference in travel time in the parallel and anti-parallel directions. This difference is noted for each sample cycle and changes from cycle to cycle can be measured and accumulated. With the 40 khz drive signals and phase reference signals employed, and a 8 mhz system frequency F, the accuracy of the measurement over 16 cycles is 200 counts per cycle times 16 Or 3200 counts total. The smallest detectable phase change divided by the largest detectable phase change in this system is 1 divided by 3200, which is quite precise.

One of the significant aspects of the signal processing according to the invention is the manner in which changes in the signal travel time between the transducers 10, 12 are tracked. In particular, whenever the result of a phase comparison measurement shows that the travel time between the transducers has changed (which can be due to either a change in flow velocity, a change in the speed of sound in the fluid or both), the launch time of the next to be transmitted acoustic burst is changed to compensate for the measured change in phase. More specifically, if the result of the phase comparison indicates that the phase of the received signal has advanced with respect to the phase reference signals (indicating that the flow velocity v, speed of sound c or both have increased since the last sample cycle), the launch time of the next transmitted signal for that transducer is retarded by an amount which reduces the advanced phase difference in the received signal to zero. Similarly, if the result of the phase comparison indicates that the flow velocity v, speed of sound c or both have decreased, signified by a receding phase difference, then the launch time of the signals from the corresponding transducer during the next cycle will be advanced by an amount required to reduce this difference to zero. In this way, each sample cycle begins with the same initial conditions: viz., if there is no change in the velocity or speed parameters since the last sample cycle the phase difference between the received signals and the phase reference signals should be zero.

FIG. 2B illustrates to an exaggerated scale the launch time adjustment after a phase comparison has resulted in a determination that the flow velocity v in the parallel direction has increased between samples. As seen in this Fig., after computation of the amount of phase difference between the received signals and the reference signals, the transmit time of the burst from transducer 10 is retarded by an amount substantially equal to the phase difference between the signals received by transducer 12 and the phase references. Similarly, the transmit time of the acoustic burst from transducer 12 is advanced by an amount equal to the phase difference between the signals received by transducer 10 (flowing in the upstream direction) and the phase reference signals. In this manner, the expected arrival time of each acoustic burst at each transducer relative to the phase reference signals and the integration interval is maintained constant.

As will now be apparent, the invention provides highly accurate measurement of the travel time of acoustic pulses between two locations in a fluid flow path. In particular, for the specific embodiment described above having a reference and drive signal frequency of 40 khz and a system clock frequency of 8 mhz, a maximum of 200 counts per cycle can be accumulated in any of the digital integrators 41-44. Since 16 successive cycles are used as the phase measurement period, a total of 3200 counts is the maximum number which could be accumulated. Consequently, the ratio between the smallest detectable phase change and the largest detectable phase change is 1 divided by 3200. Also, for a given cycle of the 40 khz signal the corresponding period is 25 microseconds, and the time between successive 8 mhz clock pulses is 125 nanoseconds, which is the lower limit on resolution of the phase difference magnitude per cycle of drive signal. Further, since the transducer drive signals must be terminated prior to the expected arrival time of a pulse at a given transducer, the programmable timers 13, 14, which are used to derive the drive signals from the relatively high frequency system clock 26, can also be used to generate the phase reference signals, which saves hardware costs. Also, since the entire system is under control of the microprocessor unit 25, computational changes and frequency changes can be relatively easy to implement.

The algorithm employed with the digital integrators 41-44 of the FIG. 1 system for a spirometer application is relatively simple. If P equals the composite phase measurement, R equals the real (in-phase) component of P and Q is the quadrature phase component of P, then the following rules may be applied in order to obtain the composite phase measurement:

If $R \geq 0$ or $Q = 0$, then $P = Q$
If $R < 0$ and $Q > 0$, then $P = Q - 2R$
If $R < 0$ and $Q < 0$, then $P = Q + 2R$ The first inequality covers the range of phase from $-90°$ to $+90°$; the intermediate inequality covers the phase range from $+90°$ to $+180°$; and the last inequality covers the range from $-90°$ to $-180°$. It should be understood that this algorithm is by way of example only, and that other algorithms may be employed, as desired.

A specific emboidment of the invention used as a spirometer is shown in the Appendix hereto.

While the above provides a full and complete disclosure of the preferred embodiments of the invention, various modifications, alternate constructions and equivalents will occur to those skilled in the art. In particular, other system frequencies than those described above can be used depending on the requirements of a given application. Therefore, the above description should not be construed as limiting the invention, which is defined by the appended claims.

What is claimed is:

1. A method of determining the travel time of an acoustic wave in a fluid, said method comprising the steps of:
   (a) generating a pair of bursts of acoustic waves at two different locations in a fluid medium;
   (b) establishing a phase reference;

(c) receiving each burst at a location different from the generation location for that burst;

(d) comparing portions of each received burst with the phase reference to determine the phase therebetween;

(e) selecting a phase value for each burst to be next generated in each location which reduces any phase difference determined in step (d) to substantially zero; and (f) using the result of step (d) to determine the travel time.

2. The method of claim 1 wherein each burst has a predetermined frequency.

3. The invention of claim 1 wherein the portion of a given burst compared in step (d) comprises N cycles of the burst frequency, where N is an integer.

4. The method of claim 3 wherein said N cycles are successive cycles.

5. The method of claim 1 wherein said step (b) of establishing includes the step of establishing a pair of references in quadrature phase; and wherein said step (d) of comparing includes the step of comparing the received burst portion with said pair of references.

6. A system for determining the travel time of an acoustic wave in a fluid, said system comprising:

transducer means for generating successive pairs of bursts of acoustic waves at two different locations in a fluid medium and for receiving said bursts after travel through said fluid medium;

means for establishing a phase reference;

means for comparing portions of each received burst with the phase reference to determine the phase therebetween;

means for selecting a phase value for each burst to be next generated by said transducer means which reduces any phase difference between the received burst portion and the phase reference to substantially zero value; and means for storing the phase determination result obtained by the comparing means.

7. The invention of claim 6 wherein said phase reference establishing means includes means for generating a pair of references in phase quadrature.

8. The invention of claim 7 wherein said comparing means includes means for comparing portions of each received burst with each of said pair of phase quadrature references.

9. The invention of claim 6 wherein said comparing means includes phase detector means having a first input coupled to said phase reference establishing means, a second input coupled to said transducer means, and an output, and means coupled to said output of said phase detector means for generating an accumulated value representative of said phase difference.

10. The invention of claim 9 wherein said phase detector means includes a pair of phase detector circuits; and wherein the second input of each of said pair of phase detector circuits receives a different one of said pair of bursts from said transducer means.

11. The invention of claim 10 wherein said transducer means includes a pair of transducers each positioned at a different one of said two different locations; and wherein each of said pair of phase detector circuits is coupled to a different one of said pair of transducers.

12. The invention of claim 6 wherein said phase reference establishing means comprises oscillator means for generating a relatively high frequency clock signal, and programmable timer means coupled to said oscillator means for generating a phase reference signal.

13. The invention of claim 12 wherein said programmable timer means includes first and second programmable timer circuits for generating a pair of phase reference signals in phase quadrature.

14. The invention of claim 12 wherein said programmable timer means includes means for generating a transducer drive signal having a frequency matched to said acoustic waves; and further including means for periodically coupling the output of said programmable timer means to said transducer means to generate said pairs of bursts.

15. The invention of claim 14 wherein said transducer means includes a pair of transducers each positioned at a different one of said two different locations; wherein said programmable timer means includes first and second programmable timer circuits for generating a pair of said transducer drive signals; and wherein said coupling means includes a pair of switch means each coupled between an associated one of said programmable timer circuits and an associated one of said pair of transducers for periodically supplying the transducer drive signal from the associated programmable timer circuit to the associated transducer.

16. A system for detecting fluid flow along a fluid path, said system comprising:

first and second transducer means for transmitting and receiving acoustic bursts through a fluid along the fluid path, one of said transducer means being positioned adjacent a first location in said fluid path, the other one of said transducer means being positioned adjacent a second location in said fluid path spaced from said first location, each said transducer means being arranged to receive the acoustic bursts transmitted by the other transducer means and travelling through said fluid path and to convert the received bursts to equivalent burst signals;

means for generating a plurality of system signals including a pair of phase reference signals in phase quadrature and drive signals for said first and second transducer means;

means for periodically coupling said drive signals to said first and second transducer means;

means coupled to said transducer means and said generating means for comparing the equivalent burst signals from said first and second transducer means to said pair of phase reference signals to determine the phase difference therebetween;

feedback means coupled to said comparing means and said generating means for adjusting the phase of said drive signals to reduce the determined phase difference to a value of substantially zero; and means for computing the value of the fluid flow along said fluid path between said first and second transducer means from the determined phase difference between the received bursts and said pair of phase reference signals.

17. The invention of claim 16 wherein said drive signals have a predetermined frequency; and wherein said coupling means includes switch means for coupling said drive signals to said first and second transducer means for a predetermined drive period.

18. The invention of claim 17 wherein said predetermined drive period has a value greater than a predetermined number N of drive signal cycles, where N is an integer, and less than a preselected travel time for an acoustic burst between said first and second locations.

19. The invention of claim 18 wherein said comparing means includes means for performing the phase comparison for N consecutive cycles of said equivalent burst signals.

20. The invention of claim 16 wherein said comparing means includes a first phase detector having a first input coupled to said generating means for receiving one of said pair of phase reference signals, and a second input coupled to the output of said first transducer means;

a second phase detector having a first input coupled to said generating means for receiving the other one of said pair of phase reference signals, and a second input coupled to the output of said first transducer means;

a third phase detector having a first input coupled to one of said pair of phase reference signals and a second input coupled to the output of said second transducer means; and a fourth phase detector having a first input coupled to said generating means for receiving the other one of said phase reference signals and a second input coupled to the output of said second transducer means.

21. The invention of claim 20 wherein said generating means includes means for generating a relatively high frequency system clock signal; and wherein said comparing means further includes first accumulating means having an enabling input coupled to the output of said first phase detector and a count input coupled to said clock signal generator for accumulating a stored value representative of the phase difference between one of said phase reference signals and the equivalent burst signals from said first transducer means; second accumulating means having an enabling input coupled to the output of said second phase detector and a count input coupled to said clock signal generator for accumulating a stored value representative of the phase difference between the other one of said phase reference signals and the equivalent burst signals from said first transducer means; third accumulating means having an enabling input coupled to the output of said third phase detector and a count input coupled to said clock signal generator for accumulating a stored value representative of the phase difference between said one of said phase reference signals and the equivalent burst signals from said second transducer means; and fourth accumulating means having an enabling input coupled to the output of said fourth phase detector and a count input coupled to said clock signal generator for accumulating a stored value representative of the phase difference between the other one of said phase reference signals and the equivalent burst signals from said second transducer means.

22. The invention of claim 20 wherein said generating means includes means for generating a relatively high frequency system clock signal, first programmable timer means for generating one of said phase reference signals and said drive signals for said first transducer means, and second programmable timer means for generating the other one of said phase reference signals and said drive signals for said second transducer means.

23. The invention of claim 22 wherein said drive signals have a predetermined frequency; and wherein said coupling means includes first switch means for coupling the drive signals from said first programmable timer to said first transducer means for a predetermined drive period, and second switch means for coupling the drive signals from said second programmable timer to said second transducer means for a predetermined drive period.

24. The invention of claim 23 wherein said feedback means includes means for individually adjusting the phase of said drive signals output from said first programmable timer means and said drive signals output from said second programmable timer means so that said drive signals for said first transducer means are adjusted for substantially zero phase between said equivalent burst signals from said second transducer and said phase reference signals and said drive signals for said second transducer means are adjusted for substantially zero phase between said equivalent burst signal from said first transducer and said phase reference signals.

* * * * *